United States Patent [19]

Yoshida

[11] Patent Number: 4,984,886
[45] Date of Patent: Jan. 15, 1991

[54] SURFACE INSPECTION APPARATUS FOR OBJECTS

[75] Inventor: Hajime Yoshida, Tokyo, Japan

[73] Assignee: Hajime Industries Ltd., Tokyo, Japan

[21] Appl. No.: 687,478

[22] Filed: Dec. 28, 1984

[30] Foreign Application Priority Data

Jan. 26, 1984 [JP] Japan .................................. 59-12694

[51] Int. Cl.⁵ ............................................ G01N 21/88
[52] U.S. Cl. ...................................... 356/237; 358/106
[58] Field of Search ................. 356/237; 358/106, 101, 358/107; 350/412

[56] References Cited

U.S. PATENT DOCUMENTS 3,980,405 9/1976 Tatsuno et al. ...................... 355/20

*Primary Examiner*—Davis L. Willis
*Assistant Examiner*—Matthew W. Koren
*Attorney, Agent, or Firm*—Bauer & Schaffer

[57] ABSTRACT

A photo-electric conversion device is provided with an independent optical system having a lens making an image of the surface of an object to be inspected which is not flat as a flat spatial image at the front stage of the photo-electric conversion device. The photo-electric conversion device receiving the flat spatial image on its target screen produces a video signal. An inspection device for processing an output video signal is provided to judge whether the inspected surface is good or not.

7 Claims, 2 Drawing Sheets

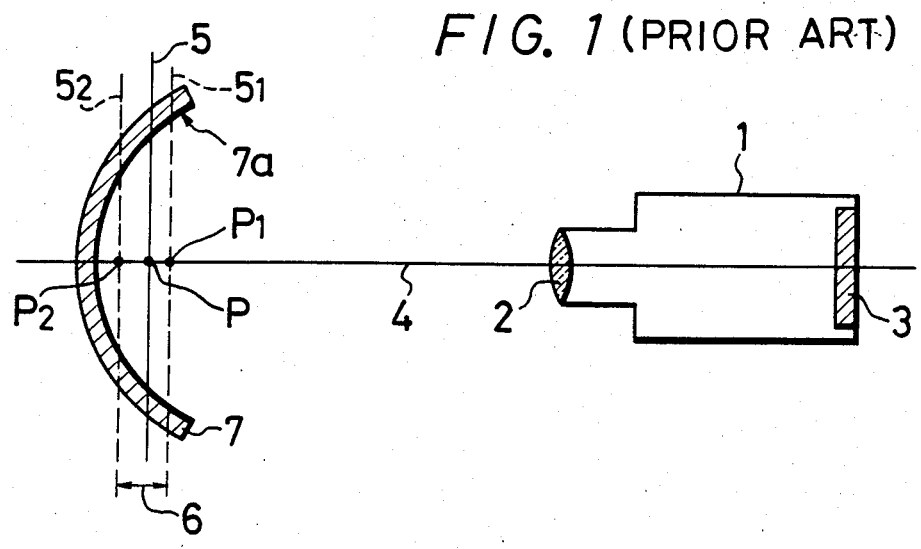
FIG. 1 (PRIOR ART)
FIG. 2 (PRIOR ART)
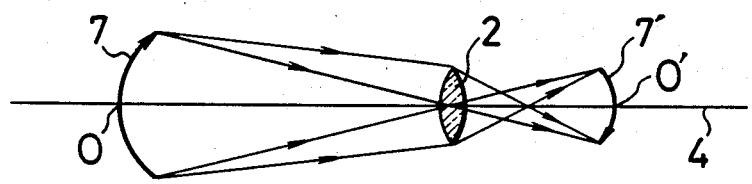
FIG. 3
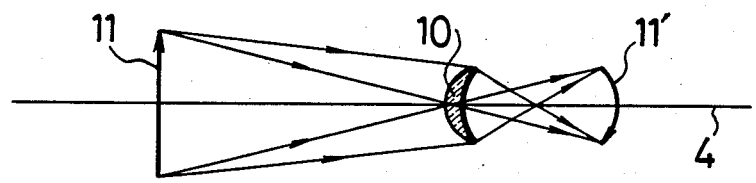
FIG. 4
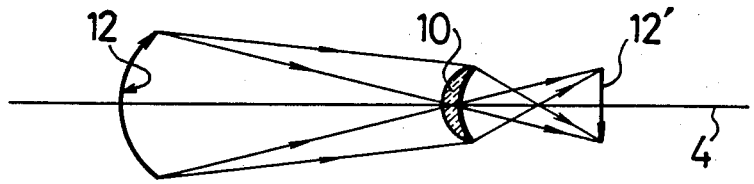

SURFACE INSPECTION APPARATUS FOR OBJECTS

BACKGROUND OF THE INVENTION

1. Field of the Invention

The present invention relates generally to apparatus for inspecting the surface of non-flat objects, and more specifically to apparatus for producing a video signal of the object for use in determining the quality of the object.

2. Description of the Prior Art

Various surface inspection apparata that use a television camera as the sensor to detect whether defects such as surface flaws exist have been proposed.

One of the television camera arrangements used at present in such systems is explained with reference to FIG. 1. In FIG. 1, a television camera used as a sensor is provided with an optical system 2 such as a convex lens and a target screen spaced along the optical axis 4. The image forming function of the optical system as used in the normal television camera 1 is, as is commonly known, able to form a clear and accurate image of only the specific area of an object 7 lying at a point P on the optical axis 4. Further, even in the event that the optical system 2 can be adjusted relative to the plane 5, it is well known that due to the so-called focal depth of the aperture stop of the optical system 2, the portion of the image within the range 6, i.e., between planes $5_1$ and $5_2$ (as shown by broken lines), each being parallel to plane 5 can be imaged substantially in focus. That is, points P1 and P2 before and after the point P on the optical axis 4, will be formed on the target screen 3 in substantially clear image. Therefore, television camera 1 is able to generate effective video signals of the objects that are within range 6.

However, if it is to be assumed that the surface 7a of the object 7 to be inspected is curved in a concave form, for example, as shown in FIG. 1 in relation to the television camera, the surface 7a includes portions that stick out on either side of the above mentioned range 6. If the conventional optical system 2 is focused to plane 5, the images of these extended portions will not be formed clearly on the target screen 3 resulting, therefore, in a so-called out-of-focus image. Accordingly, television camera 1 is not able to generate effective video signals for the extended portions at the same time that the portions within the range 6 are inspected.

It is possible to reduce the extended portion by reducing the aperture stop of the optical system 2 by which the focal depth thereof is made deeper enabling the range 6 to be enlarged behind and in front of the plane 5, but there is a limit to how far the range 6 can be spread. Depending upon the degree of curvature of the inspected surface 7a, there are many occasions where not all of the extended portions can be covered by adjusting the aperture stop of the optical system 2. Further, such reduction of the aperture stop of the optical system 2 causes a reduction of the amount of light that passes through the optical system 2. Accordingly, the amount of light that is incident on the target screen 3 of the television camera 1 is reduced, which causes the video signals to be so weak that inspection is not feasible. To avoid this, the amount of light from a light source (not indicated on the drawing) that irradiates the inspected surface 7a must be increased. However, there is also a limit to the extent to which the light may be increased so that a full concurrence to such above mentioned degree of aperture stop close down can be made.

On the other hand, it may be considered that by mounting on the television camera, a lens with a long focal length, such as a telescopic lens, the entirety of the curved inspected surface may be formed as an effective image on the target screen of the television camera without any out of focus portion. However, as is well known, when a telescopic lens is used, its focal length is so long that the television camera must be placed at some distance from the inspected object. Therefore, the use of telescopic lens on the television camera gives rise to problems of space, light source and further, due to the long focal length, as well as large disadvantageous influence arising from the shaking motions of the television camera.

In FIG. 2, another prior art arrangement is shown wherein an optical system such as convex lens 2 is used on the conventional television camera 1 so that it forms an image of a concave object 7 as an image 7' which simulates the concave object 7 although curved opposite to the object 7 as shown in FIG. 2.

In such case, if the focus of lens 2 is matched to the deepest part 0 of the object 7, the images of the other portions of the object 7 (closer portions to lens 2) will be out of focus if the focal depth is not considered. In other words, if a screen (target screen 3 of the television camera 1) is placed perpendicularly to the optical axis 4 at point 0' which corresponds to the deepest point 0 of the object 7 on the optical axis 4, the image at point 0' on the screen will be in focus, but the other portions will be all under the so-called out-of-focus condition. On the contrary, when the lens 2 focuses on the object 7 at its shallowest (foremost) portion of the image 7', at least the image at point 0' becomes out of focus.

Accordingly, the conventional surface inspection apparata that use optical systems such as those mentioned above have inevitable problems upon inspection of the non-flat surface, so that not all of the surface can be inspected at the same time.

OBJECTS AND SUMMARY OF THE INVENTION

Accordingly, an object of the present invention is to provide a surface inspection apparatus for an object that solves the above mentioned problems at one time.

According to the present invention, there is provided apparatus for inspecting an object having a non-flat surface and ascertaining whether or not the quality of the non-flat surface is acceptable as provided. The apparatus has an optical system (i.e., lens means) capable of forming a flat spatial image, of the non-flat surface of said object, in a first flat plane. This image is picked up by an image receiving means comprising a photo-electric conversion means situated in a second flat plane and a lens system for forming the focused spatial image, in the first flat plane, in a second flat plane, thereby having a flat image from which a video signal can be produced for processing.

Additional objects, features and advantages of the present invention will become apparent from the following description taken in conjunction with the accompanying drawings through which like references designate the same elements and parts.

BRIEF DESCRIPTION OF THE DRAWINGS

In the Drawings:

FIG. 1 is a schematic diagram that is used to explain the photosensing functions of a conventional television camera;

FIG. 2 is a schematic diagram also used to explain the optical system that is used in the conventional television camera;

FIG. 3 and FIG. 4 are respectively schematic diagrams that are used to explain examples of the functions of an optical system that is used in the present invention;

DESCRIPTION OF THE PREFERRED EMBODIMENTS

The present invention with the features as above mentioned will be explained hereafter in reference to FIGS. 3-7 of the drawings.

In FIG. 3, the optical system 10 having the special features and functions for use in the present invention is illustrated. Here a flat plane-like object 11 is converted on a spatial plane by the optical system 10 into a curved image 11' (in this instance, concaved facing the optical system 10).

Therefore, from the nature of light, it may be readily understood that by using the same optical system 10, a surface 12 of an object, that is concavedly curved relative to the optical system 10 can be converted into a flat image 12' on a spatial plane as seen in FIG. 4.

Figure 5:
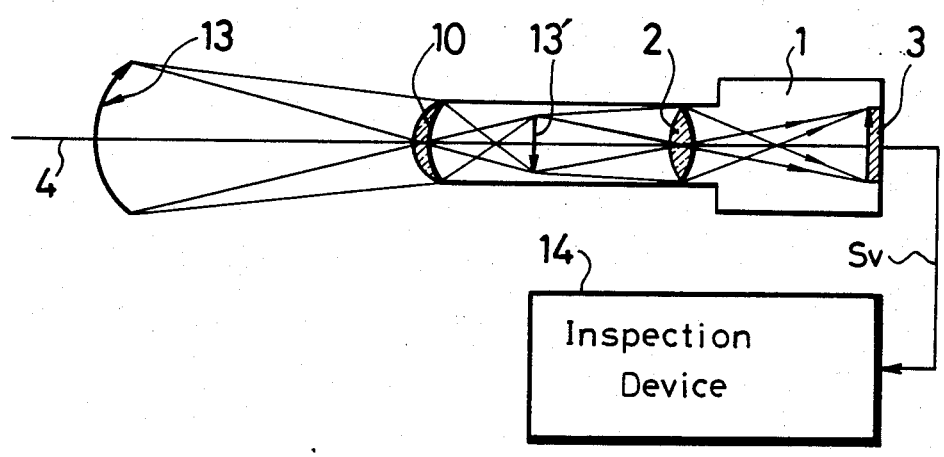
FIG. 5 is a schematic diagram showing an example of the present invention.

FIG. 5 shows an example of the surface inspection apparatus for a curved object employing the optical system 10 according to the present invention. It is noted that in FIG. 5 the like references to those used in FIG. 1 to FIG. 4 designate the same elements.

As shown in FIG. 5, an optical system 10 such as is shown in FIG. 3 and FIG. 4 is mounted to the front stage of the conventional optical system 2 of the television camera 1 as a kind of a relay lens such that the optical axes 4 of both optical systems 2 and 10 are coincident with each other. In this case, the optical system 10 may be mounted in a fashion that will permit its spaced adjustment relative to the optical system 2 so that its rear stage or focal plane coincide with that of the front stage of the television camera's optical system. The remaining construction of the television camera 1 is substantially the same as the conventional television camera as shown in FIG. 1. Also, in FIG. 5, a known inspection processing apparatus 14, such as a computer is arranged to receive and conduct a predetermined inspection procedure by processing the output image signal Sv from television camera 1.

The operation of the example of the present invention as shown in FIG. 5 will be explained. When a surface 13 of an object to be inspected is, for instance, concave-shaped facing the optical system 10 as shown in FIG. 5, an optical system having the same optical function as that shown in FIG. 3 and FIG. 4 is used. As explained in reference to FIG. 4, by using the optical system 10, the image of the surface 13 is formed as a spatial image 13' in a substantially flat plane at the rear stage of the optical system 10 coinciding with the front stage of the conventional optical system 2. This flat spatial image 13' is subsequentially picked up by the television camera 1 and formed as an image on the target screen 3 of the television camera 1 by its optical system 2 in the usual manner. At this instance, the concave or curved surface 13 remains located in relation to the optical axis 4 such that the flat spatial image 13' formed by the optical system 10 is substantially perpendicularly situated to optical axis 4 and that such spatial image 13' is formed by the optical system 2 as an image on the target screen 3. Thus, the image of the spatial image 13' that is formed on the target screen 3 by optical system 2 will be entirely in focus. Therefore, an image or video signal Sv output from television camera 1 correctly shows the entire surface of the object 13 and is an effective image signal for the inspection process. Accordingly, by processing this image signal Sv using the conventionally known inspection computer 14, the entire surface 13 can be inspected at one time without moving the object or the camera.

Figure 6:
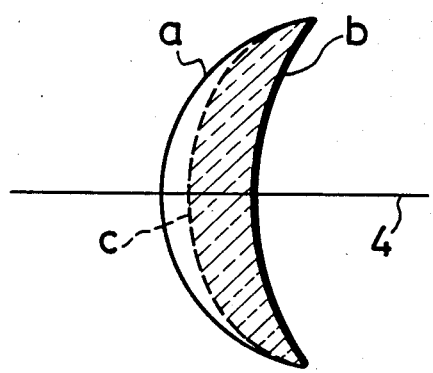
FIG. 6 and FIG. 7, respectively, are cross-sectional views showing examples of optical systems that may be used for the present invention.

A practical example of the optical system 10 (i.e., lens means) for forming an image of a non-flat surface as an image in a flat plane described as above is shown in FIG. 6. In this example, a convexo-concave lens (totally a convex or positive lens) is formed from a blank having a spherical surface b with a large radius of curvature and a spherical surface a with a small radius of curvature which is worked (i.e., ground) such that the convex spherical surface a is abraded into a non-spherical surface c such as, for instance, the flat dish-like curved surface, shown by the broken line, whereby the curvature or the degree to which the inner portion of the surface c of the optical system 10 is curved near the optical axis 4 is made gradually smaller than the curvature of the surface c about its outer peripheral portion. That is, the surface c is provided with concentric portions having different radii of curvature, the larger radius being in the concentric center while the smaller being at the periphery. Thus, the focal length of such formed optical system 10 becomes shorter further from its optical axis 4. Accordingly, the optical system 10 as shown in FIG. 6 performs the functions desired in the optical system 10 as shown in FIG. 3 to FIG. 5.

It is needless to say that the shape or radii of curvature of the non-spherical surface c as shown in FIG. 6, should be properly selected in compliance with the curved degree of the inspected surface 13 so that the image of the object can be formed as the flat plane images 12' or 13'.

Figure 7:
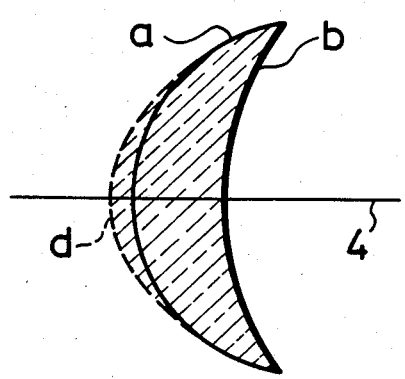

FIG. 7 shows a cross-sectional side view of another example 10' of the optical system according to the present invention. In this example, a convexo-concave lens formed with spherical surfaces a and b in the same manner as in FIG. 6 is worked such that the convex spherical surface a is shaped into a non-spherical concentric central surface d by making the degree of curvature of the surface portions a near or around the optical axis 4 larger than that of the spherical surface a about its perimeter as shown by a broken line in FIG. 7. The focal length of the lens 10' so formed becomes longer further from the optical axis 4. Therefore, by using such optical system 10', it is possible to form a flat plane image of an object which is curved opposite to that shown in FIG. 4, namely, a convex surface relative to the optical system 10'. Accordingly, this optical system 10' also accomplishes the same purpose as the optical system 10 for a convex surface. Further, the shape of the non-spherical surface d in this case may be changed in compliance with the shape of the inspected surface also.

Further the examples of FIG. 6 and FIG. 7 are cases where a so-called single lens is used, although an optical system accomplishing the above mentioned purposes may be realized by a multi-lens combination, or by a lens and prism combination, which design arrangements shall be an easy matter to those skilled in this art.

Also, while the above mentioned case is such wherein a curved surface is converted into a flat plane, the optical systems 10 or 10' may be used instead of the optical system 2 for the television camera 1, and they can be arranged so that a generally flat image of the curved inspected surface is formed directly on the target screen 3 of the television camera 1.

According to the present invention as above explained, the inspected surface of an object, which is curved to an extent that the entire surface cannot be inspected at the same time by the prior art apparatus can, in fact, be converted into a substantially flat plane surface by the special optical system, so that such a curved surface can be positively inspected wholely and at one time entirely with precision, by which the inspection efficiency may be raised with great strides.

Further, since there is no necessity to use a telescopic lens, the space for the inspection can be made small, and the conventional light source can display sufficient effects.

In addition, without escaping the scope of the novel concepts of the present invention, it is apparent that any person skilled in the art may employ many variations and changes, so that the scope of the invention should be determined by the

We claim:

1. Apparatus for inspecting an object having a non-flat surface comprising: a first optical system having lens means capable of forming a focused spatial image of the non-flat surface of said object in a first flat plane, image receiving means having photo-electric conversion means situated in a second flat plane, said image receiving means having a second optical system having lens means for forming an image, of the spatial image in said first flat plane, in said second flat plane, said photo-electric conversion means providing a signal corresponding to the focused image of the entire non-flat surface of said object in said second place, and inspection means for processing said signal to ascertain whether or not the quality of the non-flat surface of the object is acceptable.

2. The apparatus according to claim 1, in which said image receiving means comprises a television camera having integral therewith said photo-electric conversion means and said second optical system.

3. The apparatus according to claim 2, in which the lens means of said first optical system is a positive relay lens which forms a spatial image of the surface to be inspected at a position coincident with the front stage of the television camera and the lens system of said television camera forms an image of said spatial image on the target screen of said television camera.

4. The apparatus according to claim 1, in which the lens means of said first optical system comprises a convex lens having two different curved spherical surfaces.

5. The apparatus according to claim 4, in which one of said convex lens surface, facing the surface to be inspected has a shallow dish shape and another surface of said convex lens is spherical.

6. The apparatus according to claim 4, in which said convex lens is formed such that the degree of curvature of one surface facing the surface to be inspected becomes gradually smaller from the periphery of the convex lens toward its optical axis.

7. The apparatus according to claim 4, in which said convex lens is so formed that the degree of curvature of one surface facing the surface to be inspected becomes gradually larger from the periphery of the convex lens to its optical axis.

* * * * *